United States Patent
Petroski et al.

(10) Patent No.: US 12,044,665 B2
(45) Date of Patent: Jul. 23, 2024

(54) SOIL ANALYSIS COMPOSITIONS AND METHODS

(71) Applicant: Precision Planting LLC, Tremont, IL (US)

(72) Inventors: Richard Petroski, Tremont, IL (US); Rachel Nelson, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 246 days.

(21) Appl. No.: 17/375,913

(22) Filed: Jul. 14, 2021

(65) Prior Publication Data

US 2021/0341442 A1    Nov. 4, 2021

Related U.S. Application Data

(63) Continuation of application No. PCT/IB2020/050250, filed on Jan. 14, 2020.

(60) Provisional application No. 62/792,542, filed on Jan. 15, 2019.

(51) Int. Cl.
| | | |
|---|---|---|
| G01N 31/00 | (2006.01) | |
| G01N 1/40 | (2006.01) | |
| G01N 21/80 | (2006.01) | |
| G01N 31/22 | (2006.01) | |
| G01N 33/24 | (2006.01) | |

(52) U.S. Cl.
CPC ......... *G01N 31/221* (2013.01); *G01N 1/4055* (2013.01); *G01N 21/80* (2013.01); *G01N 33/24* (2013.01); *G01N 2001/4061* (2013.01); *G01N 2001/4088* (2013.01); *G01N 2033/245* (2013.01)

(58) Field of Classification Search
CPC .................................................. G01N 31/221
USPC .......................................................... 436/221
See application file for complete search history.

(56) References Cited

U.S. PATENT DOCUMENTS

| | | | |
|---|---|---|---|
| 3,853,469 A | 12/1974 | Morin et al. | |
| 3,934,977 A | 1/1976 | Cleaver | |
| 4,906,386 A * | 3/1990 | Vasconcellos | C02F 1/54 |
| | | | 210/734 |
| 5,897,834 A | 4/1999 | Lawrence et al. | |
| 6,113,856 A | 9/2000 | Lawrence et al. | |
| 2003/0044874 A1* | 3/2003 | Christner | G01N 33/66 |
| | | | 436/100 |
| 2006/0088939 A1 | 4/2006 | Rajendram | |
| 2012/0157317 A1* | 6/2012 | Tanaka | A01N 25/22 |
| | | | 504/362 |
| 2017/0254820 A1 | 9/2017 | Lange et al. | |

FOREIGN PATENT DOCUMENTS

| | | |
|---|---|---|
| CN | 2101233 U | 4/1992 |
| CN | 1081764 A | 2/1994 |
| CN | 1904598 A | 1/2007 |
| CN | 101271072 B | 11/2010 |
| CN | 102288599 A | 12/2011 |
| CN | 102 313 735 A | 1/2012 |
| CN | 104076028 A | 10/2014 |
| CN | 104076029 A | 10/2014 |
| CN | 104076121 A | 10/2014 |
| CN | 104 713 837 A | 6/2015 |
| CN | 102788791 B | 6/2015 |
| CN | 105300989 A | 2/2016 |
| CN | 206074456 U | 4/2017 |
| CN | 107727650 A | 2/2018 |
| EP | 0 432 642 A1 | 6/1991 |
| EP | 1 211 512 A2 | 6/2002 |
| GB | 2210687 B | 1/1991 |
| JP | S53003391 A | 1/1978 |
| JP | 58021163 A | 2/1983 |
| JP | 62265565 A2 | 11/1987 |
| KR | 20000000200 A | 1/2000 |
| KR | 100373109 B1 | 2/2003 |
| KR | 101833145 B1 | 2/2018 |
| WO | 97/42494 A1 | 11/1997 |
| WO | 2005/029068 A2 | 3/2005 |
| WO | 2012/087451 A1 | 6/2012 |
| WO | 2017/187282 A1 | 11/2017 |

OTHER PUBLICATIONS

Guizhi, Zhu; "Study on determination of soil soluble calcium and magnesium by chlorophosphonazo III method"; Chinese Journal of Soil Science, DOI:10319336, pp. 234-236, May 13, 1985.

Tianshou, Yin; "Study on improving turbidimetric method for soil available potassium", Analytical Methods, pp. 36-40, Dec. 31, 2012.

Tong, Wang; "Analysis of soil testing"; Jinlin Agriculture, Apr. 2012, pp. 85-86, 2012.

Rukchon et al: 11 "Development of a food spoilage indicator for monitoring freshness of skinless chicken breast", Talanta, vol. 130, Dec. 1, 2014 (Dec. 1, 2014), pp. 547-554, XP055277528, NLISSN: 0039-9140, DOI:10.1016/j.talanta.2014.07.048.

Matthieu Tubino et al: Rapid quantitative turbidimetric spot test analysis of potassium in blood serum11, Journal of the Brazilian Chemical Society, vol. 15 , No. 5, Jan. 1, 2004, pp. 635-639, XP055715547, Sao Paulo; BRISSN: 0103-5053, DOI:10.1590/50103-50532004000500004 Section: Experimental, Chemicals and Solutions, Analytical Procedures.

Ferguson J W et al: "Simultaneous Spectrophotometric Determination of Calcium and Magnesium with Chlorophosphonazo III", Analytical Chemistry, American Chemical Society, US, vol. 34, No. 4, Apr. 1, 1964, pp. 796-799, XP002617090, ISSN: 0003-2700, DOI: 10.1021/AC60210A028 Section: Experimental.

(Continued)

*Primary Examiner* — Christine T Mui
*Assistant Examiner* — Emily R. Berkeley

(57) ABSTRACT

Compositions for testing soil to measure one or more of the following properties of soil: pH, buffer pH, potassium, phosphorus, calcium, and/or magnesium. Test methods for testing soil to measure one or more of the following properties of soil: pH, buffer pH, potassium, phosphorus, calcium, and/or magnesium. A multichamber cartridge containing two or more of the compositions in separate chambers.

9 Claims, No Drawings

(56) References Cited

OTHER PUBLICATIONS

European Patent Office, International Search Report for related International Application No. PCT/I82020/050250, mail date Jul. 30, 2020.

Rao, Reddy & Takkar (1997) Malachite green method compared to ascorbic acid for estimating small amounts of phosphorus in water, 0.01 M calcium chloride, and olsen soil extracts, Communications in Soil Science and Plant Analysis, 28:6-8, 589-601, DOI: 10.1080/00103629709369813, found @http://dx.doi.org/10.1080/00103629709369813.

Ahern, Baker and Aitken, Models for relating pH measurements in water and calcium chloride for a wide range of pH, soil types and depths, Plant Soil Interactions at Low pH. 99-104, 1995 Kluwer Academic Publishers.

Baginski et al., Direct Serum Inorganic Phosphate Determination, Microchemical Journal 19, p. 285-294 (1974).

Bell et al., Development of an alternative to the Olsen bicarbonate-extraction test for determining plant-available phosphorus in basaltic soils, Soil Use and Management, vol. 21 (3) p. 330-336, Sep. 2005.

Crane, Webb, Allen & Jolley (2005) A Rapid Turbidimetric Potassium Test Modified for Use with the Pressurized Hot-Water Extraction, Communications in Soil Science and Plant Analysis, 36:19-20, 2687-2697, DOI: 10.1080/00103620500303616 found @ http://dx.doi.org/10.1080/00103620500303616.

Houba, Temminghoff, Gaikhorst & Vanvark (2000) Soil analysis procedures using 0.01 M calcium chloride as extraction reagent, Communications in Soil Science and Plant Analysis, 31:9-10, 1299-1396, DOI: 10.1080/00103620009370514, found @ http://dx.doi.org/10.1080/00103620009370514.

Feng et al., An improved malachite green assay of phosphate: Mechanism and application, Analytical Biochemistry v. 409 (2011) pp. 144-149.

Ganesh et al., Spectrophotometric determination of trace amounts of phosphate in water and soil, 2012 Water Science & Technology, 66.12, pp. 2653-2658.

Irving & Mclaughlin (1990), A rapid and simple field test for phosphorus in Olsen and Bray No. 1 extracts of soil, Communications in Soil Science and Plant Analysis, 21:19-20, 2245-2255, DOI: 10.1080/00103629009368377, found @ http://dx.doi.org/10.1080/00103629009368377.

Middleton, Elimination of Phosphate Interference in EDTA Determinations of Calcium and Magnesium in Plant Ash, Analyst, 1961, vol. 86, pp. 111-116, found @ https://doi.org/10.1039/AN9618600111.

Motomlzu, Yoshlda and Tdel, Indirect spectrophotometric determination of potassium ion in water based on the precipitation with tetraphenylborate ion and a crown ether using flow injection, Anaiytzca Chrmrca Acta, 261(1992) 225-231, Elsevier Science Publishers B V, Amsterdam.

Noda, Sato, Miura, Katayama and Kojima, Development of novel measurement assay for calcium in serum by the chlorophosphonazo-III vanadate method, Ann Clin Biochem 2010; vol. 47: pp. 440-446. DOI: 10.1258/acb.2010.010013.

Piper and Lovell, One-Step Molybdate Method for Rapid Determination of Inorganic Phosphate in the Presence of Protein, Analytical Biochemistry vol. 117, pp. 70-75 (1981).

Xing-Chu and Ying-Quani, Rapid Analysis of Cation-Exchangeable Property in Acidic III. Sensitive Spectrophotometric Determination of Microgram Amount Exchangeable Magnesium with Xylidyl Blue I in the Presence of Cetyltrimethylammonium Bromide (CTAB), Microchemical Journal vol. 33, pp. 364-370 (1986).

Sadek & Relley, Determination of Ammonium and Potassium ions in Mixtures of Alkali Metals. Use of Mercury(II) (Ethylenedinitrilo)tetraacetic Acid, Analytical Chemistry vol. 31 (4) p. 494-498, Apr. 1959.

See and Fitt, Determination of inorganic Phosphate in the Presence of Triton X-100, Analytical Biochemistry vol. 49, pp. 430-435 (1972).

Youxian, Simultaneous Spectrophotometric Determination of Calcium and Magnesium With Chlorphosphonazoiii by Flow Injection Analysis, Analytrca Chimica Acta, 212 (1988) 291-295, Elsevier Science Publishers B.V., Amsterdam.

Pflaum and Howick, Spectrophotometric Determination of Potassium with Sodium Tetraphenylborate, Analytical Chemistry, 129th meeting, ACS, Dallas, Tex., Apr. 1956.

Schall, Volumetric Determination of Potassium, Analytical Chemistry vol. 29 (7) p. 1044-1046, Jul. 1957.

Young and Gill, Determination of Magnesium in Plant Tissue with Thiazole Yellow, Analytical Chemistry vol. 23 (5) p. 751-754, May 1951.

Egorov, Nikolay et al., Influence of adding ammonium bifluoride when leaching monazite using sulphur acid, Procedia Chemistry 10 (2014), pp. 168-172.

* cited by examiner

SOIL ANALYSIS COMPOSITIONS AND METHODS

CROSS-REFERENCE TO RELATED APPLICATIONS

This application is a continuation of PCT International Application No. PCT/IB2020/050250, filed 14 Jan. 2020; which claims the benefit of U.S. Provisional Patent Application No. 62/792,542, filed on Jan. 15, 2019. The disclosure of each of the above applications are incorporated herein by reference in its entirety.

BACKGROUND

Soil analysis of agricultural fields allows a grower to know whether there are sufficient amounts of nutrients in the soil for planting. If one or more nutrients is deficient, then the nutrient can be added to soil.

Typically, soil samples are obtained via a bag and tag system in which soil samples are obtained from multiple locations in a field, placed in a bag, tagged with the information of where the soil sample was taken in the field, and then shipped to a lab for testing. This takes time, and the grower needs to wait for the test results before being able to take action.

Current soil tests are usually laborious in that soil samples are first dried to a target moisture and then ground to provide a dry soil of uniform particle size for testing. This adds processing time and costs to the testing procedure.

There are many standardized soil tests available today, such as measurement of pH with a pH meter and measurement of soil nutrients by atomic spectroscopy. These tests, however, were designed for laboratory testing, and they are not suitable for an on the go soil sampling system.

It would be desirable to test soil samples on the go with soil tests that can provide results while in the field.

BRIEF SUMMARY

In one embodiment, a composition comprising Bromocresol green and Nitrazine yellow in a weight ratio of Bromocresol green to Nitrazine yellow of 0.2:1 to 2:1.

In one embodiment, a method of measuring pH of a soil slurry comprising: a) obtaining a soil extract; b) adding Bromocresol green and Nitrazine yellow to the soil extract to form a mixture; and c) measuring absorbance of the mixture.

In one embodiment, a composition comprising methyl red and bromothymol blue in a molar ratio of 2.5:1 to 50:1.

In one embodiment, a method of measuring buffer pH of a soil slurry comprising: a) obtaining a soil extract; b) adding a buffer to the soil extract; c) adding methyl red and bromothymol blue to the buffer and soil extract to form a mixture; and d) measuring absorbance of the mixture.

In one embodiment, a composition comprising a first solution comprising sodium tetraphenylborate and a second solution comprising sodium tetraborate.

In one embodiment, a method of measuring a potassium amount of a soil slurry comprising: a) obtaining a soil extract; b) adding sodium tetraphenylborate and sodium tetraborate to the soil extract to form a mixture; and c) measuring absorbance of the mixture.

In one embodiment, a composition comprising: a first solution comprising a surfactant that forms a turbid solution in the presence of molybdate and phosphorous; and a second solution comprising a molybdate salt in a 5 to 7 N acid.

In one embodiment, a method of measuring phosphorous amount of a soil slurry comprising: a) obtaining a soil extract; b) adding a surfactant that forms a turbid solution in the presence of molybdate and phosphorous, a molybdate salt, and an acid to the soil extract to form a mixture; and c) measuring absorbance of the mixture.

In one embodiment, a composition comprising: a first solution comprising 0.5 to 0.8 mM chlorophosphonazo III, and a second solution comprising 0.04 to 0.06 M potassium hydrogen phthalate.

In one embodiment, a method of measuring calcium amount of a soil slurry comprising: a) obtaining a soil extract; b) adding chlorophosphonazo III and potassium hydrogen phthalate to the soil extract to form a mixture; and c) measuring absorbance of the mixture.

In one embodiment, a composition comprising: a first solution comprising 0.15 to 0.3 mM chlorophosphonazo III; and a second solution comprising 4 to 6.5 mM tetrabutylammonium hydroxide and 0.25 to 0.4M boric acid.

In one embodiment, a method of measuring a calcium and magnesium amount of a soil slurry comprising: a) obtaining a soil extract; b) adding chlorophosphonazo III, tetrabutylammonium hydroxide, and boric acid to the soil extract to form a mixture; and c) measuring absorbance of the mixture.

In one embodiment, a cartridge comprising at least two chambers, wherein the at least two chambers are chosen from:
- a first chamber containing a composition comprising Bromocresol green and Nitrazine yellow;
- a second chamber containing a composition comprising methyl red and bromothymol blue;
- a third chamber containing a composition comprising sodium tetraphenylborate;
- a fourth chamber containing a composition comprising sodium tetraborate;
- a fifth chamber containing a composition comprising a surfactant that forms a turbid solution in the presence of molybdate and phosphorous;
- a sixth chamber containing a composition comprising a molybdate salt in a 5 to 7 N acid;
- a seventh chamber containing a composition comprising chlorophosphonazo III;
- a eighth chamber containing a composition comprising potassium hydrogen phthalate;
- a ninth chamber containing a composition comprising tetrabutylammonium hydroxide and boric acid.

In one embodiment, a method of measuring elemental content in a soil slurry comprising: obtaining a soil extract, mixing the soil extract with water to form the soil slurry, adding a surfactant to the soil slurry; and analyzing the soil slurry for content of an element.

Accordingly, the present invention is expressly not limited to use with soil sampling at any particular location but can be used at any location.

DETAILED DESCRIPTION

The features and benefits of the invention are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

As used throughout, any ranges disclosed herein are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The compositions and methods described below can be used with on the go soil sampling systems, such as those described in U.S. Patent Publication No. US2018/0124992, or in U.S. Application Nos. 62/696,271, filed 10 Jul. 2018; 62/729,623, filed 11 Sep. 2018; and 62/745,606, filed 15 Oct. 2018. Also, the tests and methods can be used in a laboratory. When used in on the go systems, it is desirable to obtain results in a short period of time (shorter than traditional laboratory testing) so that multiple samples can be tested while traversing the field. This allows a grower to adjust application rates of nutrients in real time.

In one embodiment, the compositions and methods below can be used in a colorimetric analysis system. This allows for a minimization of testing equipment.

pH Test pH can be tested using a combination of Bromocresol green (2,6-Dibromo-4-[7-(3,5-dibromo-4-hydroxy-2-methyl-phenyl)-9,9-dioxo-8-oxa-9λ6-thiabicyclo[4.3.0]nona-1,3,5-trien-7-yl]-3-methyl-phenol, 3,3',5,5'-Tetrabromo-m-cresolsulfonphthalein Bromocresol green, CAS 76-60-8) with Nitrazine yellow (2-(2,4-Dinitrophenylazo)-1-hydroxynaphthalene-3,6-disulfonic acid disodium salt, 2-(2,4-Dinitrophenylazo)naphthol-3,6-disulfonic acid disodium salt, Nitrazol Yellow, CAS 5423-07-4). In one embodiment, there is a composition that includes Bromocresol green and Nitrazine yellow in a weight ratio of Bromocresol green to Nitrazine yellow of 0.1:1 to 100:1. In other embodiments, the weight ratio is 0.2:1 to 20:1. In one embodiment, an indicator composition having 0.01 weight % to 0.02 weight % Bromocresol green, 0.0125 weight % to 0.025 weight % Nitrazine yellow, and a liquid. A non-limiting example of the liquid is water, but other liquids can be used.

In another embodiment, the pH of a soil extract can be measured by obtaining a soil extract, adding Bromocresol green and Nitrazine yellow to the soil extract to form a mixture, and then measuring absorbance of the mixture. When used in the method, the amounts of Bromocresol green and Nitrazine yellow are not limited to the amounts in the above composition. In one embodiment, the indicator composition is added in an amount of 40 to 120 μL per mL of soil extract. In this amount, absorbance at 615 nm is increased or maximized. In one embodiment, the absorbance machine is an Agilent Cary 100 UV-Vis spectrophotometer. In one embodiment, color will develop after mixing in about 10 seconds after mixing.

The soil extract can be prepared as follows. Soil taken directly from the ground can be used without first drying and grinding. In some embodiments, the method includes adding a liquid to the soil sample to volumize the soil. A soil sample can be mixed in a 1:2 weight to weight ratio with a liquid, such as water, to form a slurry. In other embodiments, a weight ratio of soil to liquid is 1:1 to 1:5. The slurry is then mixed with a flocculating agent. Examples of flocculating agent include, but are not limited to, calcium chloride, polyacrylamide, cationic polyacrylamide, anionic polyacrylamide, polydiallyldimethyl ammonium chloride (PDADMAC), epichlorohydrin/dimethylamine copolymer (ECH/DMA), chitosan, and polyaluminum chlorides. In one embodiment, the flocculating agent is calcium chloride. In another embodiment, the flocculating agent is a combination of polyacrylamide and calcium chloride. In another embodiment, the flocculating agent is polyacrylamide. The amount of flocculating agent varies on the type of flocculating agent chosen. The flocculating agent amount can be chosen to remove organic materials and/or reduce or eliminate cloudiness. In one embodiment, a 0.017M $CaCl_2 \cdot 2H_2O$ solution is used. Alternatively, the anhydride or other hydrates of calcium chloride can be used. In one embodiment, a molar concentration for calcium chloride is 0.005M to 0.1M. The soil slurry is mixed with the flocculating agent in a volume ratio of 4:1 soil slurry:flocculating agent. In other embodiments, a volume ratio of slurry to flocculating agent is 1:1 to 10:1. In another embodiment, the calcium chloride solution can be replaced with a 0.025 weight % polyacrylamide solution. In one embodiment, the polyacrylamide can have a weight average molecular weight of 5,000,000 to 6,000,000 (CAS 9003-05-8). Other flocculating agents can be used in amounts that provide the same amount of flocculation as the above calcium chloride or polyacrylamide solutions. The soil slurry and flocculating agent are centrifuged to form the soil extract.

To convert absorbance readings to pH, an empirical correlation can be obtained as follows.

Soil samples are prepared as for typical laboratory testing by drying, crushing, and filtering to less than 2 mm particle size. Multiple samples are prepared to provide a sufficient number to generate a calibration curve. Soil is mixed in a 1:1 weight ratio with water for 5 minutes, and the pH is measured by a pH probe (an ORION™ 8103BNUWP Ross ULTRA™ pH electrode). Each of these soil samples are then processed with the above method of mixing with the flocculating agent, centrifuging, adding the indicator composition, and then measuring absorbance. The results are logged into a correlation chart and a correlation plot is obtained.

A calibration curve can be obtained and used with the correlation chart. Flocculating agent solution before adding indicator composition is measured for absorbance to establish a blank reading. The indicator composition (as described above) is then added to this sample and remeasured for absorbance. The difference in the absorbance readings is used for a calibration curve. This will provide the pH of the flocculating agent, such as the calcium chloride. This calibration can be done as needed, such as once per day. The calibration curve is used to adjust the correlation chart.

Buffer pH Test

Buffer pH can be tested using a combination of methyl red (2-{[4-(Dimethylamino)phenyl]diazenyl}benzoic acid) with bromothymol blue (4,4'-(1,1-Dioxido-3H-2,1-benzoxathiole-3,3-diyl)bis(2-bromo-6-isopropyl-3-methylphenol), CAS 76-59-5). In one embodiment, there is a composition that includes methyl red and bromothymol blue in a molar ratio of 2.5:1 to 50:1. In other embodiments, the molar ratio is 20:1 to 30:1 or about 25:1. The mixed indicator solution is made by taking 1% methyl red indicator in water and mixing it 1:1 with 0.04% bromothymol blue in a 90/10 water/ethanol mixture to make a final concentration of 0.5% methyl red, 0.02% bromothymol blue in a 95/5 water/ethanol solution by weight.

In another embodiment, the buffer pH of a soil extract can be measured by obtaining a soil extract, combining with a buffer, adding methyl red and bromothymol blue to the soil extract to form a mixture, and then measuring absorbance of the mixture. In some embodiments, the buffer is added to the soil extract before adding the methyl red and bromothymol blue. The soil extract can be prepared as described above for the soil slurry. The soil slurry can be combined with a buffer solution in a volume ratio of 4:1 slurry to buffer. In one embodiment, the volume ratio is 1:1 to 10:1. In one embodiment, the buffer solution is Sikora buffer. Sikora buffer is available from GFS Chemicals of Powell, Ohio, and it is about 85.6% water, 13.7% potassium chloride, 0.278% triethanol amine and balance minors. Optionally, a flocculating agent can be added (as described above, for example using polyacrylamide as described above) and centrifuged to form a filtrate.

When used in the method, the amounts of methyl red and bromothymol blue are not limited to the amounts in the above composition. In one embodiment, the indicator composition is added in an amount of 60 to 120 µL per mL of filtrate. In this amount, absorbance at 617 nm is increased or maximized. In one embodiment, the absorbance machine is an Agilent Cary 100 UV-Vis spectrophotometer. In one embodiment, color will develop after mixing in about 10 seconds after mixing.

To convert absorbance readings to Buffer pH, an empirical correlation can be obtained as follows.

Soil samples are prepared as for typical laboratory testing by drying, crushing, and filtering to less than 2 mm particle size. Multiple samples are prepared to provide a sufficient number to generate a calibration curve. Soil is mixed in a 1:1 weight ratio with water for 5 minutes, and the SMP (Shoemaker, McLean, and Pratt) buffer pH is measured by a pH probe (an ORION™ 8103BNUWP Ross ULTRA™ pH electrode) using the standard lab procedure for SMP buffer pH. Each of these soil samples are then processed with the above method of mixing with the buffer (e.g., Sikora buffer), centrifuging, adding the indicator composition, and then measuring absorbance. The results are logged into a correlation chart and a correlation plot is obtained.

A calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This will provide the pH of the buffer (e.g., Sikora buffer). This calibration can be done as needed, such as once per day. The calibration curve is used to adjust the correlation chart.

Potassium Analysis

Potassium can be tested using a combination of reagents including sodium tetraphenylborate, sodium tetraborate, and a polyol (such as glycerol). In one embodiment, a first solution contains 60 mM to 100 mM (or 2 weight % to 3.5 weight %) sodium tetraphenylborate in the solution, or about 87.7 mM (or 3 weight %) sodium tetraphenyl borate. A second solution contains sodium tetraborate at 0.85 mM to 1 mM (or about 0.938 mM) and 0.25 M to 0.4 M (or about 0.327 M) glycerol. In one embodiment, the composition contains about 87.7 mM (about 3 weight %) sodium tetraphenylborate, about 0.938 mM sodium tetraborate decahydrate, and 0.327 M (about 2.4 or 2.38 weight %) glycerol. Optionally, the first solution and second solution can be prepared as a single solution.

The soil extract can be prepared as follows. Soil taken directly from the ground can be used without first drying and grinding. A soil sample can be mixed in a 1:2 weight to weight ratio with a liquid, such as water, to form a slurry. In other embodiments, a weight ratio of soil to liquid is 1:1 to 1:5. The slurry can then be extracted with an extractant, such as nitric acid. In one embodiment, nitric acid concentration is 0.005 to 0.2 M. In one embodiment, a volume ratio of extractant to soil slurry is 4:1. In other embodiments, the volume ratio is 1:1 to 10:1. A benefit to using either of these extractants is that a shorter extraction time can be obtained, such as 20 seconds or less or 10 seconds or less. This allows for faster processing while testing on the go.

Optionally, a flocculating agent can be added (as described above, for example using polyacrylamide as described above, such as at 0.01 weight %) and centrifuged to form a filtrate.

Optionally, a base, such as lithium hydroxide, can be added before or after centrifuging to remove interfering materials. In other embodiments, sodium hydroxide can be used. In one embodiment, a concentration of lithium or sodium hydroxide is 0.05 to 0.2M.

The extract is then centrifuged. A sufficient amount of base is added to remove the interfering materials.

In one embodiment, the base is added after extraction. In one embodiment, the extract before the base is added and potassium concentration is diluted 25 to 35 fold by the addition of the base, the first solution, the second solution, and optional water.

The extract is then mixed with the sodium tetraphenylborate, sodium tetraborate decahydrate, and glycerol reagent. In one embodiment, the first solution is mixed with the extract with a weight ratio of extract to tetraphenyl borate of 2:1 to 1:1, optionally 1.5:1. In one embodiment, the second solution is mixed with the extract in a weight ratio of sodium tetraborate to extract of 3:1 to 6:1, optionally 5.4:1. In this amount, absorbance at 420 nm is increased or maximized. In one embodiment, color will develop after mixing in about 10 seconds after mixing. In one embodiment, the absorbance machine is an Agilent Cary 100 UV-Vis spectrophotometer. A non-limiting example of this test is described in Appendix A.

To convert absorbance readings to potassium levels, an empirical correlation can be obtained as follows.

Soil samples are prepared as for typical laboratory testing by drying, crushing, and filtering to less than 2 mm particle size. Multiple samples are prepared to provide a sufficient number to generate a calibration curve. The traditional test for potassium in soil is conducted using the ammonium acetate extraction using 1 g of soil and 10 parts of a 1M ammonium acetate solution at pH 7, mixing, filtering with filter paper, and then measuring by ICP-OES. The test can be referenced in Recommended Chemical Soil Test Procedures for the North Central Region, North Central Regional Research Publication No. 221, Missouri Agricultural Experiment Station SB 1001, August 2015. Alternatively, the Mehlich-3 extractant can be used instead of 1M ammonium acetate at pH 7. The samples are also measured using the above potassium test and the results are correlated for a correlation curve.

A calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This calibration can be done as needed, such as once per day. The calibration curve is used to adjust the correlation chart.

Phosphorus Test

Phosphorus can be tested using a combination of reagent including a surfactant, such as Triton X-100 surfactant (Polyethylene glycol p-(1,1,3,3-tetramethylbutyl)-phenyl ether, CAS 9002-93-1), and a molybdate salt, such as ammonium molybdate tetrahydrate, in an acid solution. Acids that can be used include, but are not limited to sulfuric acid, nitric acid, and hydrochloric acid. In one embodiment, an amount of Triton X-100 is 0.5 to 2 weight % of the composition. In one embodiment, the acid has a concentration of 5 to 7 N, optionally 6N. In one embodiment, the composition includes ammonium molybdate tetrahydrate in a range of 15 to 25 mM, optionally 20.2 mM, in a 5 to 7 N, optionally 6N, sulfuric acid solution. In other embodiments, sodium molybdate can be used in place of ammonium molybdate in the same molar amounts. The surfactant is one that forms a turbid composition in the presence of molybdate and phosphorous.

Optionally, a flocculating agent can be added (as described above, for example using polyacrylamide as described above, such as at 0.01 weight %).

The reagent can be added to the soil solution in a weight ratio of soil:Triton X-100:ammonium molybdate tetrahydrate of 1:26:3. After mixing, the solution will become turbid. In one embodiment, absorbance can be read after 10 seconds of mixing. Absorbance can be read via a spectrophotometer at 510 nm. In one embodiment, the absorbance machine is an Agilent Cary 100 UV-Vis spectrophotometer.

Soil samples are prepared as for typical laboratory testing by drying, crushing, and filtering to less than 2 mm particle size. Multiple samples are prepared to provide a sufficient number to generate a calibration curve. The traditional test for phosphorus in soil is conducted using the Bray-1 or the Bray-2 extractants, and then measuring by ICP-OES. The test can be referenced in Recommended Chemical Soil Test Procedures for the North Central Region, North Central Regional Research Publication No. 221, Missouri Agricultural Experiment Station SB 1001, August 2015. The samples are also measured using the above phosphorus test and the results are correlated for a correlation curve.

A calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This calibration can be done as needed, such as once per day. The calibration curve is used to adjust the correlation chart. A non-limiting example of this test is in Appendix B.

Calcium Test

Calcium can be tested using a combination of chlorophosphonazo III (Bis(4-chloro-2-phosphonobenzolazo) chromotropic acid, CAS 1914-99-4) and potassium hydrogen phthalate (CAS 877-24-7). In one embodiment, the composition has a pH of 3.5 to 4.5, and in one embodiment, the pH is about 4. The sample color change is proportional to the calcium concentration in the sample. In one embodiment, a first solution is 0.04 to 0.06 M potassium hydrogen phthalate, optionally 0.05M, and a second solution is 0.5 to 0.8 mM, optionally 0.66 mM, chlorophosphonazo III. Optionally, the first solution and second solution can be prepared as a single solution.

The soil extract can be prepared as follows. Soil taken directly from the ground can be used without first drying and grinding. A soil sample can be mixed in a 1:2 weight to weight ratio with a liquid, such as water, to form a slurry. In other embodiments, a weight ratio of soil to liquid is 1:1 to 1:5. Soil is extracted using a 1M ammonium acetate at a pH of about 7 in a slurry:extractant volume ratio of about 1:4. In other embodiments, the volume ratio is 1:1 to 1:10. In this combination, extraction time is about 10 seconds. In other embodiments, nitric acid can be used. The mixture is centrifuged, and an aliquot is taken. Depending on the expected amount of calcium, the mixture can be diluted with water in an amount such that the calcium concentration is in the range of the sensing method. For example, this range can be 200-5,000 ppm calcium.

The aliquot is mixed with a combination of chlorophosphonazo III and potassium hydrogen phosphate at a pH of about 4. Absorbance at 665 nm is then read. In one embodiment, the absorbance instrument is an Agilent Cary 100 UV-Vis spectrophotometer. A non-limiting example of this test is described in Appendix C.

Soil samples are prepared as for typical laboratory testing by drying, crushing, and filtering to less than 2 mm particle size. Multiple samples are prepared to provide a sufficient number to generate a calibration curve. The traditional test for calcium in soil is conducted by extracting the sample with 1M ammonium acetate and then measuring by ICP-OES. The test can be referenced in Recommended Chemical Soil Test Procedures for the North Central Region, North Central Regional Research Publication No. 221, Missouri Agricultural Experiment Station SB 1001, August 2015. The samples are also measured using the above calcium test and the results are correlated for a correlation curve.

A calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This calibration can be done as needed, such as once per day. The calibration curve is used to adjust the correlation chart.

Magnesium Test

Magnesium can be tested by testing a combined amount of magnesium and calcium and then subtracting the calcium. The combined amount can be tested using a combination of tetrabutylammonium hydroxide (CAS 2052-49-5), boric acid, and chlorophosphonazo III. In one embodiment, a first solution contains 0.15 to 0.3 mM, optionally 0.219 mM, chlorophosphonazo III, and a second solution contains 4 to 6.5 mM, optionally 5.4 mM, tetrabutylammonium hydroxide with 0.25 to 0.4 M, optionally 0.323 M, boric acid. In one embodiment, the second solution has a pH of 6.5 to 7.5, and in one embodiment, the pH is about 7, which is adjusted with boric acid or Tetrabutylammonium hydroxide as needed. Optionally, the first solution and second solution can be prepared as a single solution. The sample color change is proportional to the magnesium and calcium concentration in the sample.

The soil extract can be prepared as follows. Soil taken directly from the ground can be used without first drying and grinding. A soil sample can be mixed in a 1:2 weight to weight ratio with a liquid, such as water, to form a slurry. In other embodiments, a weight ratio of soil to liquid is 1:1 to 1:5. Soil is extracted using a 1M ammonium acetate at a pH of about 7 in a slurry:extractant volume ratio of about 1:4. In other embodiments, the volume ratio is 1:1 to 1:10. In this combination, extraction time is about 10 seconds. In other embodiments, nitric acid can be used. The mixture is centrifuged, and an aliquot is taken. Depending on the expected amount of magnesium, the mixture can be diluted with water in an amount such that the calcium concentration is in the range of the sensing method. For example, this range can be 50-500 ppm magnesium.

The aliquot is mixed with a combination of tetrabutylammonium hydroxide (CAS 2052-49-5), boric acid, and chlorophosphonazo III at a pH of about 7. Absorbance at 669 nm is then read. In one embodiment, the absorbance instrument is an Agilent Cary 100 UV-Vis spectrophotometer. Non-limiting examples of this test are described in Appendix D1 and Appendix D2.

Soil samples are prepared as for typical laboratory testing by drying, crushing, and filtering to less than 2 mm particle size. Multiple samples are prepared to provide a sufficient number to generate a calibration curve. The traditional test for magnesium in soil is conducted by extracting the sample with 1M ammonium acetate and then measuring by ICP-OES. The test can be referenced in Recommended Chemical Soil Test Procedures for the North Central Region, North Central Regional Research Publication No. 221, Missouri Agricultural Experiment Station SB 1001, August 2015. The samples are also measured using the above magnesium test and the results are correlated for a correlation curve.

A calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This calibration can be done as needed, such as once per day. The calibration curve is used to adjust the correlation chart.

Cartridge

In one embodiment, a multichamber cartridge can be provided in which each chamber contains one of the above compositions in a combination that tests for at least two of the above listed tests (e.g., two or more of the pH test, buffer pH test, potassium test, phosphorous test, calcium test, and/or magnesium tests). In one embodiment, the cartridge has a chamber for the pH test composition, a chamber for the buffer pH test composition, a chamber for the potassium test composition, a chamber for the phosphorous test composition, a chamber for the calcium test composition, and a chamber for the magnesium test composition. In one embodiment, any of the cartridges can contain an additional chamber that does not contain any of the compositions for the above tests.

EXAMPLES

Example 1—Potassium Analysis

A first experiment was performed to test potassium analysis of soil. Water used in reagent preparation or analysis is type 1 water. The experiment of this example uses the following components:

Solution A: Tetraphenylborate 3%; 3 g per 100 mL of 0.08 N NaOH.

Solution B: Combined reagent

Sodium tetra borate decahydrate FW=381.4 Weigh 300.4 mg and transfer the powder into a 1-liter plastic bottle, containing 500 mL of water.

Add 40 mL of a commercial 50% (v/v) glycerol in water (Ricca Chemical): Glycerol is very viscous. Measure the glycerol with a glass cylinder. Rinse the graduate cylinder several times with water (total additional water is 300 mL) and add this to the solution above. The total volume of this solution is 840 mL.

The preparation of standards used test tubes, and most soils fall between 50 and 300 µg of K per gram of soil; this is 50 to 300 ppm. The preparation of standards used a standard solution of 50 ppm of K corresponds to 40.0 µL, 70.0 µL and 100 µL, for standards with total potassium levels of 2, 3.5 and 5 µg per ml (2, 3.5 and 5 ppm). The preparation of standards brought the standard solutions to 100 µL with water and add 100 µL of 0.03 N nitric acid. The total volume should be 200 µL for all standards.

The experiment included the following methodology: extracted soil in a 1:10 soil to extractant ratio with 0.03 M $HNO_3$ for 2 minutes then centrifuge, then took a 100 µL aliquot of the sample and add 100 µL of water to each sample in test tubes. The volume for each sample should be 200 µL, which is the same as for the standards.

Adding 100 µL of 0.10 M LiOH into each test tube, containing either standards or samples, and mix. Store LiOH solution under argon atmosphere. Adding 200 µL of Reagent A and mix. Turbidity appears. Adding 2.70 mL of reagent B and mix. The final volume is about 3.20 mL. Transfer to plastic cuvettes and read at 420 nm. Turbidity continues to develop until 10-15 minutes, but the standards and samples can be read earlier than that if they are all read within the same time frame. Read the standards and samples at 420 nm against water blanks in the Cary 100 UV-Vis instrument. From this calibration curve, the sample results should be multiplied by 100 to obtain the soil ppm of K.

Example 2—Phosphorus Analysis

A second experiment was performed to test phosphorus analysis of soil. Water used in analysis is type 1 water. The experiment of this example uses the following components:

Solution A 1% weight/volume Triton X-100; 1 gram per 100 mL water

Solution B Ammonium molybdate; 2.5 grams of ammonium molybdate tetrahydrate is dissolved in 100 mL of 6N sulfuric acid (60 mL of 10 N sulfuric acid is added to 40 mL of water).

The preparation of standards used soil test results to get the amount of phosphorus in soils. This is a range of 1 to 50 µg per gram of soil for Bray 1 extract (weak Bray) and a range of 10 to 150 for Bray 2 (strong Bray). Using 100 mg of soil the amount of phosphorus is one tenth of the above values in the soil sample. For example, 50 µg per gram P in soil gives 5 µg in the 100 mg soil sample. Use 1 mL of Bray 1 for routine analysis, to measure the amount of P available to the plant and 1 mL of Bray 2, to estimate the stored P (in the "bank" for the plant when made available by microbes in the soil). A 200 µL aliquot of the soil extract would have on fifth of the total extracted phosphate.

The standard preparation further used a stand stock solution of 6 µg per mL to prepare standards. Aliquots would be 0, 50, 100 and 200 µL for 0, 0.3, 0.6 and 1.2 µg of phosphorus. Bring a/l standard volumes to 200 µL total with water.

The standard preparation further used 200 µL of soil extract for Bray 1 analysis and 100 µL of soil extract for Bray 2 analysis. The dilution factor for Bray 1 analysis is 50-1 and the dilution factor for Bray 2 analysis is 100-1.

The standard preparation further used samples, blanks and samples should have the same amount of Bray 1 or Bray 2 extractant (200 µL for Bray 1 and 100 µL for Bray 2), then added water to bring the total volume to 2.7 mL.

The experiment included the following methodology: added 30 µL of Reagent A, 1% Triton X-100, to the samples blank and standards and then mixed and wait 2 minutes. Subsequently, added 300 µL of Reagent B, 2.5% Ammonium molybdate in 6 N sulfuric acid. Mix and wait up to 20 min for the turbidity to develop. The absorbances at 510 nm were then read, using the CONCENTRATION feature of the Cary 100 instrument. The amount of total phosphorus in the soil is the concentration times the dilution factor used.

Example 3—Calcium Analysis

A third experiment was performed to test calcium analysis of soil. For this test, calcium is determined at near pH 4 with chlorophosphonazo III as the colorimetric reagent. All water used is type 1. The experiment of this example uses the following components:
   0.05 M Potassium hydrogen phthalate (KHP) This is near pH 4
   10.21 g KHP per liter of water
   2.041 g KHP per 200 mL water
   Chlorophosphonazo III (CPA)
   0.5 mg per mL in water
   For example, 10 mg CPA in 20 mL water
   Calcium standard stock solution, 100 µg per mL water
   Dilution of Agilent ICP standard solution (1000 µg per mL=1000 ppm) 1 to 10 dilution Just prior to analysis, dilute the Ca standard stock solution 1 to 10. The resulting solution is 10 µg per mL.

To create a Ca standard graph, 0, 40 µL, 80 µL and 120 µL of the diluted Ca standard solution were used, which contains 0, 0.4 µg, 0.8 µg and 1.2 µg Ca in the standards. All standards are brought to 120 µL with water for the analysis. The resulting graph is nearly linear; only slight deviation from linearity is observed at the 1.2 µg data point.

Soil samples are extracted with a tenfold volume of 0.01 N nitric acid (10 mL per gram of soil). The extract is diluted 1 to 10 with water. For unknown soils, two analyses were performed; one using 40 µL of the diluted extract and another using 80 µL of the diluted extract. Sample volumes are brought to 120 µL with water.

A colorimetric analysis was performed—whereby the CPA solution can be added to the buffer and used as a single reagent. For this the following was used:
   Sample or standard 120 µL
   0.05 M KHP solution 2750 µL
   CPA solution 250 µL
   Total volume 3.12 mL. This volume facilitates transfer of the solution to the cuvettes.

The standards and samples were read at 665 nm. The standards provide a linear graph of absorbance as a function of Ca concentration.

Subsequently, the blank absorbance value was subtracted from the 0.8 µg data point absorbance. This value was divided by 0.8 to give the absorbance per 1 µg of calcium for soil samples with an absorbance corresponding 0.1 µg of Ca or less in the sample.

The blank absorbance value was subtracted from the 1.2 µg data point absorbance. This value divided by 1.2 to give the absorbance per jig Ca for soils with an absorbance corresponding to an absorbance greater than 1 µg Ca in the sample up to about 1.3 µg Ca in the soil sample. The 40 µL sample should be used, instead of the 80 µL sample size, when the Ca values exceed the linear range.

These calcium determination values are used as a reference for the actual amount of Ca in a subsequent analysis at pH 7.0 that measures the amount of calcium and magnesium together. The magnesium value is calculated from the total (Ca plus Mg) minus the amount of Ca in the sample (absorbance measured at pH 7.0, using the magnesium determination CPA method).

Example 4—Magnesium+Calcium Analysis

A fourth experiment was performed to test magnesium and calcium analysis of soil. For this test, magnesium is determined at pH 7 with chlorophosphonazo III as the colorimetric reagent. All water used is type 1. The experiment of this example uses the following components:
   Tetrabutylammonium hydroxide (TBAH) solution (40% in water) 0.72 mL approx. 0.72 g.
   Boric acid 4.0 g. Add to 200 mL of water. The pH is adjusted to 7 with either boric acid or TBAH.
   Chlorophosphonazo III 16.6 mg per 100 mL water The extractant used for this analysis is 1 M ammonium acetate (AA). Each standard needs to have the same amount of AA.

This experiment used the following standards:
   Working water solution: 100 µL of AA added to 900 µL of water
   Working Magnesium standards: 100 µL of 200 ppm Mg standard stock solution, 100 µL of AA, and 800 µL of water. This yields a final Mg standard of 20 ppm
   Working Calcium standards: 100 µL of 500 ppm Ca standard stock solution, 100 µL of AA, and 800 µL of water. This yields a final Ca standard of 50 ppm For calibration curves the following methodology was used: creating a Mg standard graph, using 0, 10 µL, 20 µL, and 30 µL of the working Mg standard solution. All standards are brought to 150 µL with the working water solution for the analysis. The resulting graph is linear.

For calibration curves the following methodology was used: creating a Ca standard graph, use 0, 20 µL, 40 µL, and 80 µL of the working Ca standard solution. All standards are brought to 150 µL with the working water solution for the analysis. The resulting graph is linear.

For colorimetric analysis, the following methodology was used: samples are extracted with 1 M ammonium acetate for 2 minutes. Each sample was diluted 1:10 with water and then a 50 µL aliquot is used for the colorimetric determination. Each sample has 50 µL 1:10 sample with 100 µL of the working water solution to yield a final volume of 150 µL. The absorbance obtained is the Mg+Ca absorbance.

The colormetric analysis included the following characteristics:
   Standards/Sample: 150 µL
   Water: 1800 µL
   pH 7 Buffer: 600 µL
   CPA solution: 600 µL
   Total volume 3.15 mL. This volume facilitated transfer of the solution to the cuvettes.

The standards and samples were read at 669 nm on the Cary 100 UV-Vis instrument and the resulting calibration curve is linear for Mg and Ca. The dilution for the Mg+Ca analysis was 6300. The Mg was determined by subtraction from the Ca determination at pH 4. Using the Ca at pH 7 calibration curve resulted in the absorbance of Ca in the sample and then subtracted that absorbance from the sample absorbance at pH 7. A "zero calibration curve" was created by subtracting all of the Mg calibration curve values by the blank calibration curve absorbance. The subtracted sample absorbance at pH 7 was subtracted from the "zero calibration curve" to obtain the amount of Mg present in the sample. The value obtained by the curve should be multiplied by 6300 to get the ppm Mg in soil.

Example 5—Magnesium Determination

A fifth experiment was performed to test magnesium determination for reference Mg standards and Mg determination in soils. For this test, magnesium is determined at pH 7 with chlorophosphonazo III as the colorimetric reagent.

All water used is type 1. The experiment of this example uses the following components:

Tetrabutylammonium hydroxide (TBAH) solution (40% in water) 0.72 mL approx. 0.72 g Boric acid 4.0 g. Add to 200 mL of water. The pH is adjusted to 7 with either boric acid or TBAH.

Chlorophosphonazo III (CPA) 16.6 mg per 100 mL in water

Magnesium standard stock solution, 40 μg per mL water

Dilution of Agilent ICP standard solution (1000 μg per mL=1000 ppm) 1 to 25 dilution.

Just prior to analysis, the Mg standard stock solution was diluted 1 to 20. The resulting solution is 2 μg per mL.

To create a Mg standard graph, use 0, 50 μL, 100 μL, and 150 μL, of the diluted Mg standard solution, which contains 0, 0.10 μg, 0.20 μg and 0.30 μg Mg in the standards. All standards are brought to 150 IA, with water for the analysis. The resulting graph is linear.

The colormetric analysis included the following characteristics:

Standards 150 μL
Water 1800 μL
pH 7.0 buffer 600 μL
CPA solution 600 μL
Total volume 3.15 mL, which facilitates transfer of the solution to the cuvettes.

The standards were read at 669 nm. The standards provided a linear graph of absorbance as a function of Mg concentration. The blank absorbance value was subtracted from the 0.10 μg data point absorbance. This value gives the absorbance per 0.1 μg of magnesium found in soil samples. Alternatively, the absorbance of the 0.10 μg data point was subtracted from the absorbance of the 0.20 μg data point.

These magnesium determination values were used as a reference for the actual amount of Mg in a subsequent analysis (under the same conditions for this analysis) that measures the amount of calcium and magnesium together, in the soil sample.

The methodology further included recalling the actual amount of Ca in the soil sample, determined at pH 4. This amount of calcium was added to a test tube. This Ca is used as a standard for the analysis at pH 7, using the above procedure.

A soil sample was analyzed for total calcium plus magnesium at pH 7 as described above. The magnesium value was calculated from the total (Ca plus Mg) in the soil sample, minus the amount of Ca only. The absorbance of the calcium only, at pH 7, was subtracted from the absorbance of the amount of Ca plus Mg, found in the soil sample at pH 7.

The invention claimed is:

1. A method of measuring pH of a soil slurry comprising:
   a. obtaining a soil extract which comprises a flocculating agent;
   b. adding Bromocresol green and Nitrazine yellow in a weight ratio of Bromocresol green to Nitrazine yellow of 0.1:1 to 100:1 to the soil extract that includes the flocculating agent to form a mixture;
   c. measuring absorbance of the mixture; and
   d. determining a pH of the mixture based on the measured absorbance.

2. The method of claim 1, wherein a weight ratio of Bromocresol green to Nitrazine yellow is 0.1:1 to 20:1.

3. The method of claim 1, wherein the soil extract is prepared by:
   a. obtaining a soil sample;
   b. adding a liquid to the soil sample to volumize the soil sample;
   c. mixing the liquid and soil sample to form a soil slurry;
   d. filtering the soil slurry;
   e. adding the flocculating agent to the soil slurry; and
   f. centrifuging the soil slurry to form the soil extract.

4. The method of claim 3, wherein the liquid is water, and a weight ratio of soil sample to water is 1:1 to 1:5.

5. The method of claim 1, wherein the Bromocresol green and the Nitrazine yellow are added as a composition, the composition comprising 0.01 to 0.02 weight % of Bromocresol green and 0.0125 to 0.025 weight % of Nitrazine yellow.

6. The method of claim 3, wherein the flocculating agent is selected from calcium chloride, polyacrylamide, cationic polyacrylamide, anionic polyacrylamide, polydiallyldimethyl ammonium chloride, epichlorohydin/ethylamine copolymer, chitosan, polyaluminum chloride, or a combination of two or more thereof.

7. The method of claim 6, wherein the flocculating agent comprises polyacrylamide, calcium chloride, or a combination thereof.

8. The method of claim 6, wherein the flocculating agent is added in an amount such that the volume ratio of soil slurry to flocculating agent is 1:1 to 10:1.

9. The method of claim 3, wherein preparing the soil extract does not include an addition of an acid.

\* \* \* \* \*

UNITED STATES PATENT AND TRADEMARK OFFICE
CERTIFICATE OF CORRECTION

PATENT NO. : 12,044,665 B2
APPLICATION NO. : 17/375913
DATED : July 23, 2024
INVENTOR(S) : Richard Petroski et al.

Page 1 of 1

It is certified that error appears in the above-identified patent and that said Letters Patent is hereby corrected as shown below:

In the Claims

Column 14, Claim 6, Line 4, replace "epichlorohydin/ethylamine" with "epichlorohydrin/dimethylamine".

Signed and Sealed this
Fifteenth Day of July, 2025

Coke Morgan Stewart
*Acting Director of the United States Patent and Trademark Office*